United States Patent
Standar

(10) Patent No.: US 8,111,805 B2
(45) Date of Patent: Feb. 7, 2012

(54) CLUTCH AND MAMMOGRAPHY DEVICE

(75) Inventor: Robert Standar, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 360 days.

(21) Appl. No.: 12/275,904

(22) Filed: Nov. 21, 2008

(65) Prior Publication Data

US 2009/0143146 A1 Jun. 4, 2009

(30) Foreign Application Priority Data

Nov. 28, 2007 (DE) .......................... 10 2007 057 287

(51) Int. Cl.
*A61B 6/02* (2006.01)

(52) U.S. Cl. ........................................................ 378/37

(58) Field of Classification Search .................... 464/36; 378/37
See application file for complete search history.

(56) References Cited

U.S. PATENT DOCUMENTS

| 865,486 | A | * | 9/1907 | Gannon | .......................... | 464/36 |
| 2,600,674 | A | | 6/1952 | Natkins | | |
| 3,199,644 | A | | 8/1965 | Clapp | | |
| 3,220,526 | A | * | 11/1965 | Gattiker, Jr. | ................ | 464/36 X |
| 4,226,316 | A | * | 10/1980 | Geisthoff | ..................... | 464/36 X |
| 5,526,394 | A | * | 6/1996 | Siczek et al. | ..................... | 378/37 |

FOREIGN PATENT DOCUMENTS

| DE | 843 776 C | | 7/1952 | | |
| DE | 2056962 | | 8/1971 | | |
| DE | 24 33 995 A1 | | 2/1975 | | |
| DE | 31 20 303 A1 | | 10/1982 | | |
| DE | 40 40 702 A1 | | 6/1992 | | |
| JP | 2-134420 A | * | 5/1990 | ...................... | 464/36 |

OTHER PUBLICATIONS

German Office Action dated Nov. 18, 2008 with English translation.

* cited by examiner

*Primary Examiner* — Gregory Binda

(74) *Attorney, Agent, or Firm* — Lempia Summerfield Katz LLC

(57) ABSTRACT

A clutch with a first clutch disk and a second clutch disk is provided. The first clutch disk includes at least one cylindrical shaft, in which a sphere is mounted in a displaceable fashion in each instance so as to press against a spring. The second clutch disk, which, for each shaft of the first clutch disk, includes a recess for partially receiving a sphere.

16 Claims, 3 Drawing Sheets

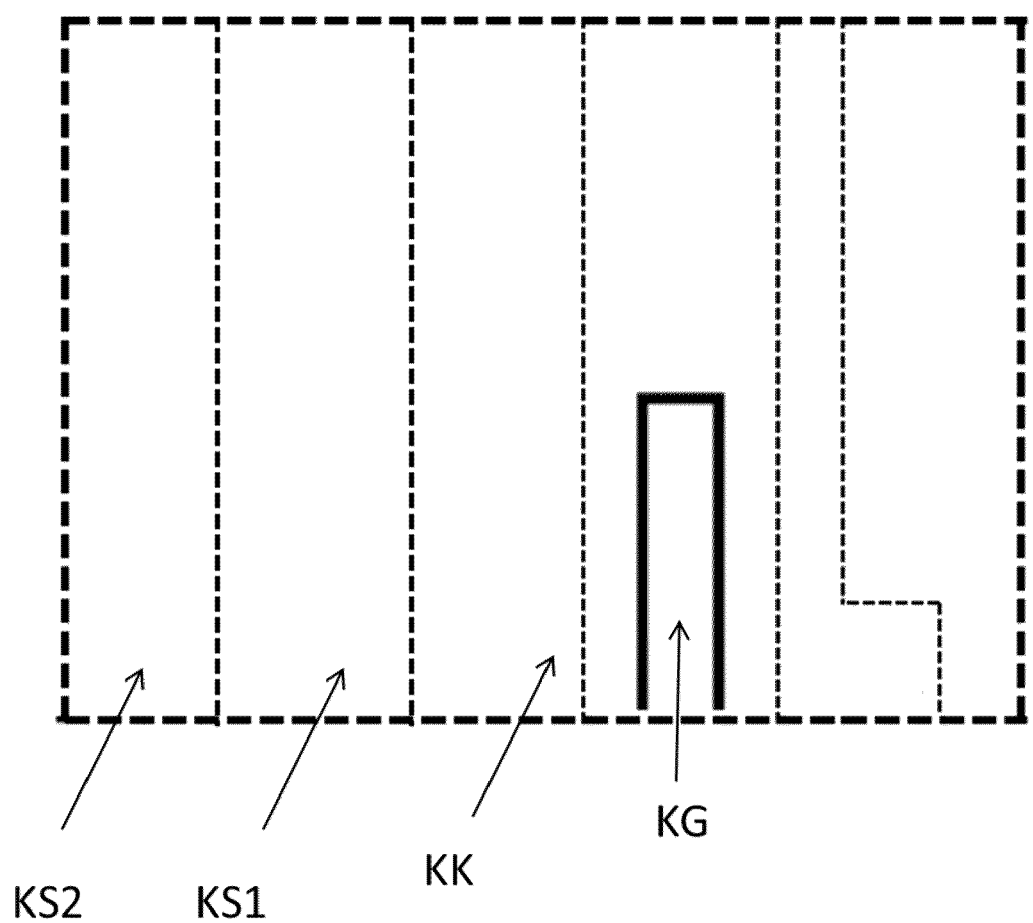

CLUTCH AND MAMMOGRAPHY DEVICE

The present patent document claims the benefit of the filing date of DE 10 2007 057 287.7, filed Nov. 28, 2007, which is hereby incorporated by reference.

BACKGROUND

Design engineers, in differing areas of technology, are faced with deploying clutches that correspond to the respective situation and which allow simple but effective and reliable transmission of power between a drive motor and a gear mechanism or between different parts of a motorized drive system. The solution is a function of the requirements of the situation with regard to mechanical loading capacity, safety, operating capacity and similar criteria.

When constructing mammography devices, for example, a motorized compression aid, which is not able to exert compression forces above 200 Newtons, is used. In this process, the compression force must be maintained in the event of a power outage and it must be ensured that the compression force can be manually canceled.

With known compression units, the overload protection is realized, for example, by a shear pin in the form of a clamping sleeve. When the overload protection shears, the compression unit is, however, unusable and is replaced. In the event of a power outage, the compression force can in any event be manually cancelled by a hand wheel.

SUMMARY

The present embodiments may obviate one or more of the problems or drawbacks inherent in the related art. For example, in one embodiment, a clutch is provided. The clutch includes a first clutch disk with at least one cylindrical shaft, in which a sphere is mounted in a displaceable fashion in each instance so as to press against a spring in each instance and with a second clutch disk, which, for each shaft of the first clutch disk, is in each instance equipped with a recess for partially receiving a sphere.

BRIEF DESCRIPTION OF THE DRAWINGS

FIG. 5 illustrates one embodiment of a mammography device showing a jaw clutch arranged downstream of the clutch.

DETAILED DESCRIPTION

Figure 1:
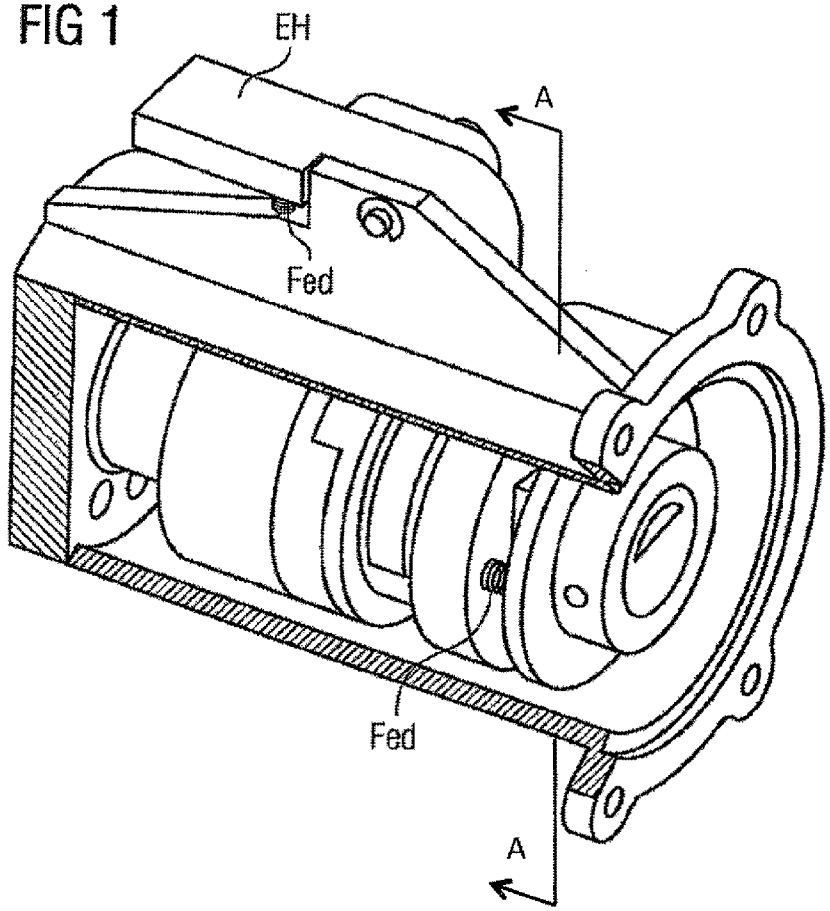
FIG. 1 illustrates one embodiment of a clutch.
Figure 2:
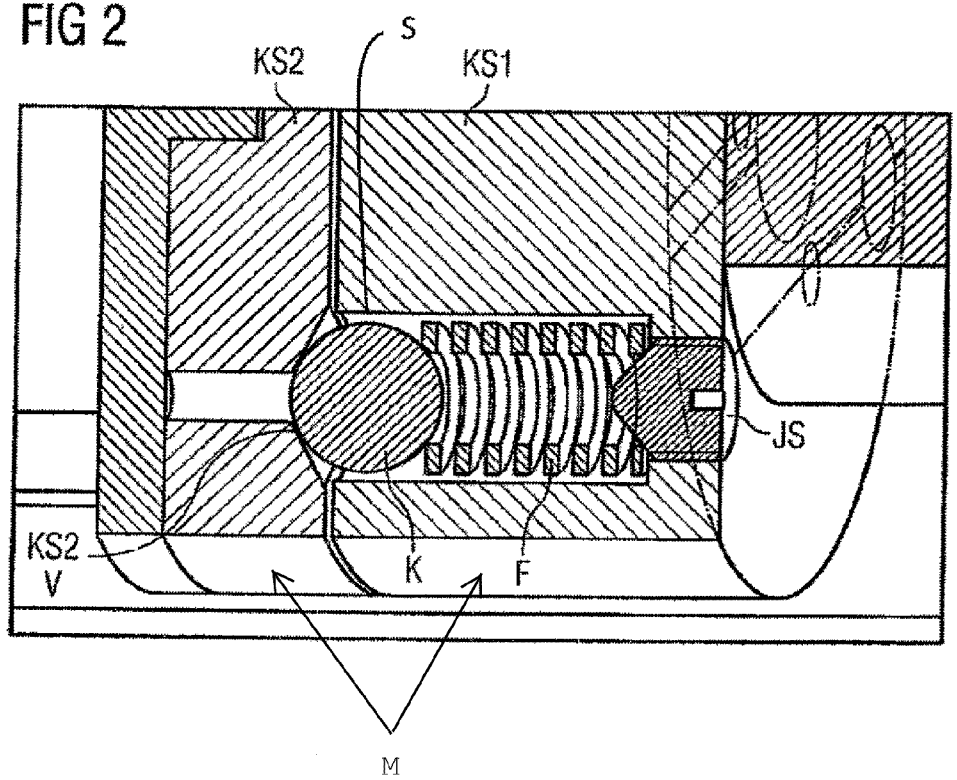
FIG. 2 illustrates one embodiment of a sectional image of a clutch along direction A-A of FIG. 1.

FIG. 1 illustrates a compression unit of a mammography device. The person skilled in the art in other areas of technology easily identifies on the basis of the present descriptions how the invention can be applied to different areas of technology.

In one embodiment, a clutch is provided with a first clutch disk (KS1) having at least one cylindrical shaft (S), in which a sphere (K) is mounted in a displaceable fashion in each instance so as to press against a spring (F) and with a second clutch disk (KS2), which, for each shaft (S) of the first clutch disk (KS1), is equipped with a recess (V) for partially receiving a sphere (K) in each instance.

The clutch may be equipped with adjusting screws (JS) on the shaft ends facing the sphere in each instance.

Figure 3:
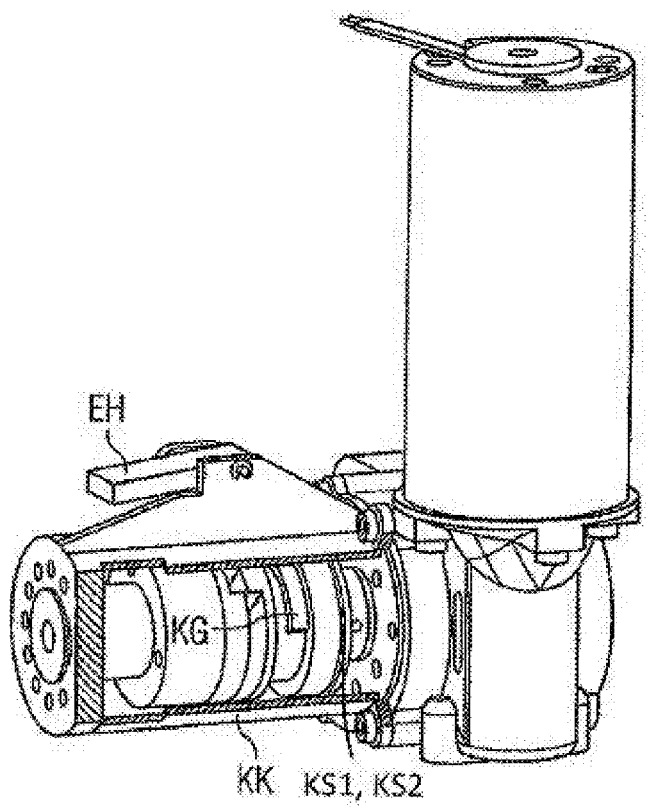
FIG. 3 illustrates one embodiment of a motor in an unlocked state.
Figure 4:
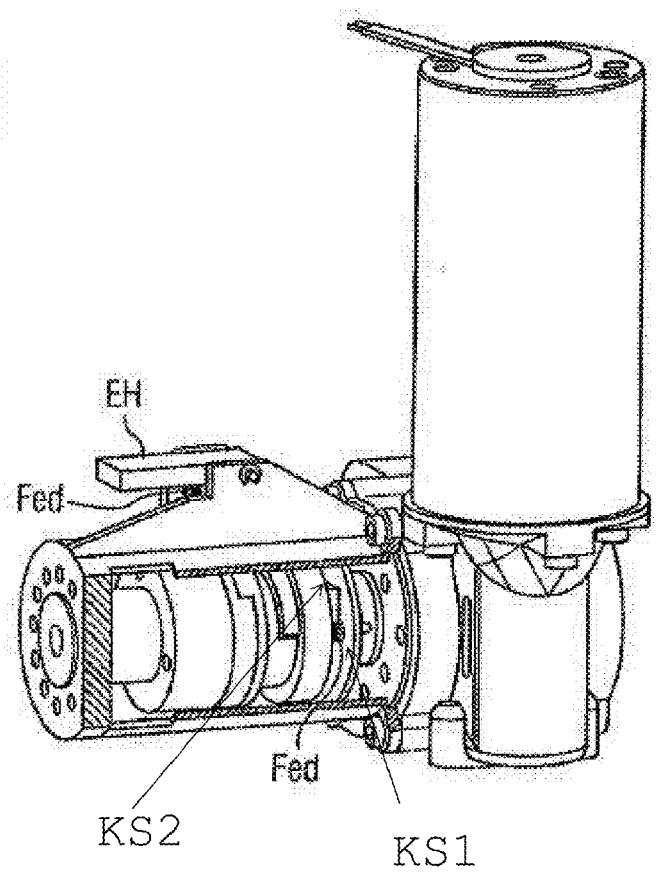
FIG. 4 illustrates one embodiment of a clutch with a motor in the locked state.

The clutch may include a jaw clutch (KK) arranged upstream (FIGS. 1, 3, and 4) or downstream (FIG. 5) thereof, which can be unlocked with the aid of a clutch fork (KG) that may be pivoted in the axial direction with the aid of an unlocking lever (EH).

A mammography device with a motorized compression aid (M) may include a clutch.

The safety clutch and the emergency release are preferably flanged directly on the drive motor. With the inventive safety clutch, the compression force of up to 200 Newton is preferably transmitted by springs (F) and steel spheres (K). In the event of an overload, the spring-loaded spheres (K) unlatch from the depressions (V) and the force closure is broken. The releasing force may be adjusted by headless screws (JS).

In one embodiment, two, preferably hardened clutch disks (KS1, KS2) are connected in a force-fit fashion by way of a three sprung spheres (K). The sprung spheres (K) may be adjusted to the required torque and thus the maximum admissible compression force by way of adjusting screws (JS).

If the torque is to lie above the adjusted value, the spheres (K) are pushed out of their counter bearing (V) and the force fit is lost. Accordingly, a disk of the clutch may rotate freely and no force is transmitted to the further device parts, for example, in the mammography device on the compression plate.

In the event of a power outage, a jaw clutch (KK) can be unlocked by actuating the emergency release. Accordingly, the clutch and thus the additional device parts, such as the compression plate in a mammography device, is relieved of the compression force. The displacement of the compression plate etc. by hand is now possible.

In one embodiment, a compact unit may include a motor, safety clutch, and an emergency release in an assembly. After the response of the safety clutch, this automatically reengages after 120 degrees for the transmission of force of up to 200 Newton. The compression unit and the safety clutch are then completely functional again.

The emergency release is actuated by way of a button (e.g. the unlocking lever EH), which cannot be actuated unintentionally. With continuous actuation of the button (EH), the compression plate or such like can be lifted as quickly as possible into any desired position. By releasing the button (EH), the compression plate reengages immediately via the jaw clutch and the compression plate is fixed to this position.

The invention claimed is:

1. A mammography device comprising:
   a motorized compression aid having a clutch, the clutch comprising:
     a first clutch disk having at least one cylindrical shaft, in which a sphere is mounted in a displaceable fashion so as to press against a spring; and
     a second clutch disk having a recess for partially receiving the sphere of the at least one cylindrical shaft; and
   a jaw clutch arranged upstream of the first clutch disk and the second clutch disk.

2. The mammography device of claim 1, further comprising adjustable screws facing the sphere on an end of the at least one cylindrical shaft.

3. The mammography device of claim 1, wherein the clutch is movable between a locked position and an unlocked position.

4. The mammography device of claim 3, wherein when the clutch is in the unlocked position, at least a portion of the jaw clutch is connected to or engaged with the first clutch disk and the second clutch disk.

5. A mammography device comprising:
   a motorized compression aid having a clutch, the clutch comprising:
      a first clutch disk having at least one cylindrical shaft, in which a sphere is mounted in a displaceable fashion so as to press against a spring; and
      a second clutch disk having a recess for partially receiving the sphere of the at least one cylindrical shaft; and
   a compression plate adjacent the first clutch disk.

6. The mammography device of claim 5, wherein the sphere and the spring are configured to transmit a compression force on the compression plate.

7. The mammography device of claim 6, wherein the compression force is less than 200 Newtons.

8. The mammography device of claim 6, further comprising adjustable screws facing the sphere on an end of the at least one cylindrical shaft.

9. The mammography device of claim 8, wherein the adjustable screws are configured to provide a releasing force on the spring and the sphere, and wherein the releasing force is equal to a maximum admissible compression force on the compression plate.

10. The mammography device of claim 9, wherein the adjustable screws are configured to release the sphere from the recess when the compression force exceeds the releasing force.

11. The mammography device of claim 5, wherein the spring is made of steel.

12. The mammography device of claim 11, wherein the sphere and the spring are configured to transmit a compression force on the compression plate.

13. The mammography device of claim 12, wherein the compression force is less than 200 Newtons.

14. The mammography device of claim 5, wherein the at least one cylindrical shaft includes three sprung spheres.

15. The mammography device of claim 5, further comprising a jaw clutch arranged upstream of the first clutch disk and the second clutch disk.

16. The mammography device of claim 5, further comprising a jaw clutch arranged downstream of the first clutch disk and the second clutch disk.

* * * * *